United States Patent [19]

Arretz

[11] Patent Number: 5,312,993
[45] Date of Patent: May 17, 1994

[54] PROCESS FOR THE MANUFACTURE OF DIMETHYL DISULPHIDE

[75] Inventor: Emmanuel Arretz, Pau, France

[73] Assignee: Elf Atochem S.A., Paris, France

[21] Appl. No.: 970,592

[22] Filed: Oct. 29, 1992

Related U.S. Application Data

[63] Continuation of Ser. No. 664,698, Mar. 5, 1991, abandoned.

[30] Foreign Application Priority Data

Mar. 5, 1990 [FR]  France ................... 0902715

[51] Int. Cl.$^5$ .......................................... C07C 321/14
[52] U.S. Cl. ........................................ 568/26; 568/21
[58] Field of Search ..................... 568/26, 21

[56] References Cited

U.S. PATENT DOCUMENTS 3,277,180 1/1964 Bapseres et al. .................. 568/26
3,314,999 11/1963 Bapseres et al. .................. 568/26
4,876,389 10/1989 Gongora et al. .

FOREIGN PATENT DOCUMENTS 269517 6/1988 European Pat. Off. .

OTHER PUBLICATIONS

Hougen et al., *Chemical Process Principles,* Part III, pp. 1028–1029, (1961).

Primary Examiner—Marianne M. Cintins
Assistant Examiner—Margaret J. Page
Attorney, Agent, or Firm—Morgan & Finnegan

[57] ABSTRACT

The invention relates to the manufacture of dimethyl disulphide from methyl mercaptan and sulphur. The process according to the invention is characterized in that it comprises:
(a) a first reaction zone in which the methyl mercaptan and sulphur are introduced and reacted in the presence of a catalyst,
(b) a degassing zone in which the products originating from the first reaction zone are treated to remove at least partially the dissolved hydrogen sulphide, and
(c) a second reaction zone in which the products originating from the degassing zone are brought into contact with a catalyst.

9 Claims, 1 Drawing Sheet

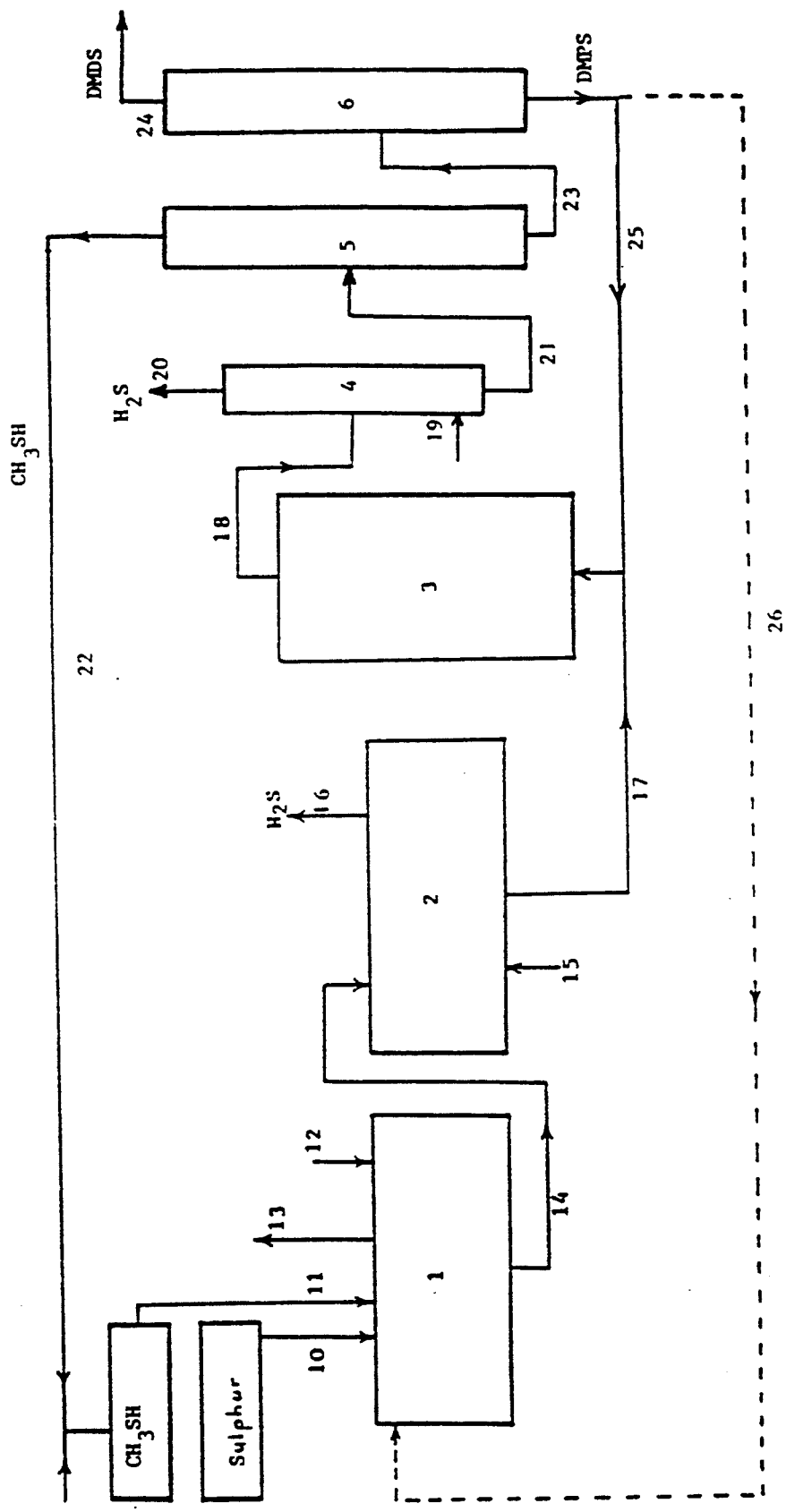

PROCESS FOR THE MANUFACTURE OF DIMETHYL DISULPHIDE

This is a continuation of co-pending application Ser. No. 07/664,698, filed on Mar. 5, 1991 now abandoned.

FIELD OF THE INVENTION

The present invention relates to a new process for the manufacture of dimethyl disulphide.

BACKGROUND OF THE INVENTION

An important access route to organic disulphides consists of the oxidation of mercaptans with sulphur in the presence of a catalyst.

When a mercaptan (RSH) and sulphur are brought into contact with a catalyst, the corresponding disulphide is obtained according to the following reaction scheme:

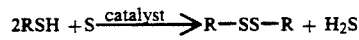
$$2RSH + S \xrightarrow{catalyst} R-SS-R + H_2S$$

using one sulphur atom S per two molecules of mercaptan.

The formation of the disulphide R—SS—R is generally accompanied by the formation of secondary products, namely polysulphides of analogous structure to the disulphide, but containing a larger number of combined sulphur atoms ($R-S_n-R$ with $n>2$).

The reactions which lead to the polysulphides can be denoted by the following equations:

$$2RSH + xS \xrightarrow{catalyst} R-S_n-R + H_2S \ (x > 1 \text{ and } n = x + 1)$$

$$R-SS-R + yS \xrightarrow{catalyst} R-S_n-R \ (y \geq 1 \text{ and } n = y + 2)$$

It is known that polysulphides ($R-S_a-R$) can be converted into disulphides (R—SS—R) by reaction with the mercaptan RSH. These reactions may be denoted as follows:

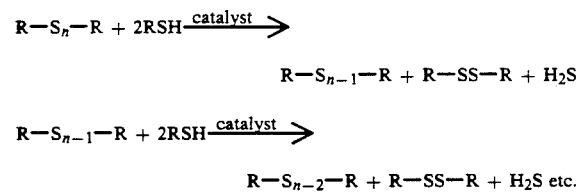
$$R-S_n-R + 2RSH \xrightarrow{catalyst}$$
$$R-S_{n-1}-R + R-SS-R + H_2S$$
$$R-S_{n-1}-R + 2RSH \xrightarrow{catalyst}$$
$$R-S_{n-2}-R + R-SS-R + H_2S \text{ etc.}$$

In the case where the polysulphides are completely converted to disulphides, the general equation for this conversion can be outlined as follows:

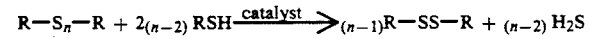
$$R-S_n-R + 2_{(n-2)} RSH \xrightarrow{catalyst} {}_{(n-1)}R-SS-R + {}_{(n-2)} H_2S$$

This reaction of conversion of a polysulphide to disulphide has been exploited in U.S. Pat. No. 3,299,146 in a process for the preparation of dimethyl disulphide, which consists in reacting methyl mercaptan with dimethyl trisulphide:

$$CH_3-SH_3-CH_3 + 2\ CH_3SH \rightarrow 2\ CH_3-SS-CH_3 + H_2S$$

The processes for continuous manufacture of dialkyl disulphides from alkyl mercaptans and sulphur, which are described in European Patent No. 202,420 and European Patent No. 337,839 make use of a synthesis reactor in which the mercaptan and sulphur are introduced. The polysulphides formed in the reaction of oxidation of the mercaptan with sulphur are separated from the disulphides by distillation, then they are recycled to the synthesis reactor to be converted to disulphide. This continuous recycling results in increasing the amount of polysulphides in the reactor and in decreasing the disulphide yield, as well as making needful a distillation column with sizes and characteristics adapted to reaction product compositions rich in polysulphides. For the manufacture of dimethyl disulphide from methyl mercaptan and sulphur, the examples of the above-cited cited European patents show readily that the synthesis reactor produces rather large amounts of dimethyl polysulphides.

DESCRIPTION OF THE INVENTION

According to the present invention which relates to a specific process for the manufacture of dimethyl disulphide from methyl mercaptan and sulphur, it has now been found that it is much more advantageous to perform the reaction of conversion (or of reversion) of dimethyl polysulphides to dimethyl disulphide in an independent reactor, the yields under these conditions being much greater than in the case of recycling to the synthesis reactor. Moreover, it has been found that the presence of hydrogen sulphide in the reactants introduced into the reversion reactor has an unfavorable effect on the efficiency of conversion of dimethyl polysulphides to dimethyl disulphide and that the prior removal of hydrogen sulphide enables virtually complete conversions to dimethyl disulphide to be achieved.

The process according to the invention for the manufacture of dimethyl disulphide from methyl mercaptan and sulphur is characterized in that it comprises two reaction zones and an intermediate degassing zone.

The first reaction zone is fed with reactants (methyl mercaptan and sulphur) which, in the presence of a catalyst (optionally introduced simultaneously with the reactants) react together to give the dimethyl disulphide and dimethyl polysulphides.

The degassing zone is situated downstream of the first reaction zone and its purpose is to remove the hydrogen sulphide present in the liquid crude products leaving the first reaction zone. Although it is preferred to remove hydrogen sulphide as completely as possible, it would not constitute a departure from the scope of the present invention to remove only a proportion (at least 50%) of the hydrogen sulphide. This degassing operation can be performed either by heating the products or by entrainment with an inert gas, optionally combined with heating at a pressure above atmospheric pressure to 10 bars, preferably below 6 bars.

The second reaction zone, fed with products originating from the degassing zone after removal of at least 50% of the hydrogen sulphide, is for the purpose of converting the dimethyl polysulphides to dimethyl disulphide by reaction with the methyl mercaptan in the presence of catalyst.

BRIEF DESCRIPTION OF THE DRAWING

In the attached figure, which is not considered to limit the invention, the diagrammatic illustration of an embodiment of the new process for the manufacture of dimethyl disulphide comprises a first reactor 1 (primary reactor), a degasser 2, a second, additional reactor 3 (finishing reactor), a degassing column 4 for complete removal of hydrogen sulphide from the reaction products before distilling them, and a distillation section 5 and 6.

DETAILED DESCRIPTION OF THE INVENTION

The reactants: sulphur (liquid or solid) and methyl mercaptan (liquid), which is in excess relative to the stoichiometry, are introduced into the reactor 1 via conduits 10 and 11 respectively. In the case where the reaction catalyst is incorporated simultaneously, it is introduced via conduit 12. The gaseous effluents which may form in the reactor are optionally removed via conduit 13, and the liquid crude reaction product drawn off from the reactor 1 is conveyed by the conduit system 14 to the degasser 2. The residence time in the reactor 1 is controlled in a manner which is known per se so as to obtain at its exit a virtually complete conversion of the sulphur initially introduced, that is to say a conversion of 100% or at least such that the unconverted sulphur may dissolve in the liquid effluent.

The degasser 2 is equipped for removing selectively via conduit 16 the hydrogen sulphide dissolved in the liquid which originates from the reactor 1, either by heating or by entrainment with an inert gas introduced via conduit 15.

The liquid freed from hydrogen sulphide is drawn off a the bottom of the degasser and is conveyed via the conduit system 17 to the finishing reactor 3, in which the dimethyl polysulphides formed in the reactor 1 are converted into dimethyl sulphide in the presence of catalyst by reaction with the excess methyl mercaptan. The residence time in the reactor 3 is controlled in a manner which is known per se as a function of the dimethyl polysulphide content which is accepted in the effluent, a longer residence timing promoting the reversion of dimethyl polysulphides to dimethyl disulphide.

The products leaving the reactor 3 are conveyed by the conduit 18 to the degassing column 4 for complete removal of the dissolved hydrogen sulphide, either by heating or by entrainment with an inert gas introduced via conduit 19.

The distillation section is fed by the conduit system 21 with products leaving the degassing column 4 for the separation in column 5 of the methyl mercaptan present in the product with a view to its being recycled to the reactor 1 by the conduit system 22. The product recovered at the bottom of column 5 is conveyed via the conduit system 23 to the column 6 at the head of which the dimethyl disulphide is recovered via the conduit system 24, while the column 6 tailings, consisting of unconverted dimethyl polysulphides mixed with dimethyl disulphide, are preferably recycled to the finishing reactor 3 via the conduit system 25. A possible alternative form consists in returning the tailings from column 6 to the reactor 1 via the conduit system 26 shown using broken lines in the attached figure.

The device described above corresponds to the simplest embodiment. A person skilled in the art will understand that it would not constitute a departure from the scope of the present invention to use a first reaction zone consisting of a number of reactors operating in parallel and connected to the same degasser or to a plurality of degassers forming an intermediate degassing zone.

Similarly, it would not constitute a departure from the scope of the present invention to use a second reaction zone consisting of a number of finishing reactors. Thus, for example, to improve the dimethyl disulphide yield and to avoid dimethyl polysulphide recycling, a number of finishing reactors arranged in series can be used, each preceded by an intermediate degasser permitting the removal of the hydrogen sulphide formed in the preceding reactor.

The process according to the invention can be used with reactors of different types, for example stirred and/or tubular ones, the choice of which will depend on the reaction conditions and on the nature of the catalysts employed.

As in known processes, the methyl mercaptan/sulphur molar ratio must be at least 2. Since a large excess of methyl mercaptan promotes the selectivity for dimethyl disulphide, the mercaptan/sulphur molar ratio may be between 2 and 10, and is preferably between 3 and 6, to minimize the quantity of methyl mercaptan needing to be separated off and recycled.

In each reaction zone, the reaction is conducted at pressures above atmospheric pressure. The pressure should be sufficient to maintain the methyl mercaptan in the liquid state and may be up to 50 bars.

The process according to the invention may be employed in a wide temperature range, depending on the nature of the catalysts employed. In the case of thermally stable catalysts the temperature may be between 25° C. and 150° C.

Any of the catalysts known in the prior art for oxidizing mercaptans with sulphur may be employed in the new process according to the invention, regardless of whether they are liquid or solid organic or inorganic basic agents, such as alkaline bases, alkali-metal alcoholates, alkali metal mercaptides, combinations of alkaline bases with a mercaptan and an alkene oxide, amines in the free state or fixed on organic supports (organic anion exchange resins), or whether they are inorganic oxides of some metals, like magnesium oxide, or aluminosilicates like zeolites. The catalysts in the two reaction zones may be identical or optionally different.

Given the technical and economic advantages represented by the use of sulphur in liquid form when it is introduced into the synthesis reactors, the choice of the catalyst may determine the type of primary reactor (reactor 1 in the attached figure) to be used in the process according to the invention.

In the case where catalysts of limited thermal stability are employed, such as anion exchange resins containing tertiary amine functional groups such as, for example, Amberlyst A21, IRA 93 SP and IRA 94 S, whose temperature resistance does not exceed 100° C., the introduction of liquid sulphur (melting temperature of sulphur from approximately 113° C.) involves the use of a stirred reactor, in which the catalyst is in suspension in the liquid medium, as a primary reactor (reactor 1 in the attached figure). The reaction between the methyl mercaptan and sulphur must be carried out at a temperature below 100° C. in the presence of these resins as catalysts.

In the case where the catalysts employed are solids whose mechanical resistance to attrition is low, the use of a stirred reactor as a primary reactor (reactor 1 in the attached figure) should be avoided. Insofar as these catalysts are thermally stable, their use in a stationary-bed tubular reactor as a primary reactor (reactor 1 in the attached figure) is the most appropriate technical solution, it being necessary for the reaction temperature in this case to be above the melting temperature of sulphur.

In the case where homogeneous and stable liquid catalysts are employed, the primary reactor (reactor 1 in the attached figure) may be either of stirred type or of tubular type. Catalysts of this type are introduced into the primary reactor simultaneously with the methyl mercaptan and sulphur reactants and, in this case, it serves as catalyst in the finishing reactor (reactor 3 in the attached figure) of the process according to the invention, which may be either of stirred type or of tubular type.

On the other hand, in the case where the primary reactor (reactor 1 in the attached figure) contains a charge of solid catalyst which is insoluble in the reaction mixture, the solid catalyst employed in the finishing reactor (reactor 3 in the attached figure) may be identical or different. Depending on the nature of the catalyst used, the finishing reactor 3 may be of stirred or tubular type; in the case of a solid catalyst with low resistance to attrition, the reactor will be preferably tubular with a stationary bed.

EXAMPLES

The following examples illustrate the invention without limiting it.

EXAMPLE 1 (comparative)

A. Continuous synthesis of dimethyl disulphide from methyl mercaptan and sulphur The synthesis reactor, of stirred type, is equipped with a central stirrer, liquid methyl mercaptan and liquid sulphur feeds, a pneumatic pressure-control valve and a system for discharging liquid enabling a constant volume to be maintained in the reactor.

The reaction volume is set at 300 cm$^3$.

Tests were carried out with two different catalysts: an anion exchange resins (Amberlyst A21) and an amine (triethylamine). The reactants are introduced in a methyl mercaptan/sulphur molar ratio of 4, the methyl mercaptan with a flow rate of 960 g/h and the sulphur with a flow rate of 160 g/h. The pressure in the reactor is 5.5 bars gauge and the reaction temperature is 40° C.

For the tests with Amberlyst A21 resin, the predried charge which is employed is 20 g. For tests with triethylamine, the amine is introduced into the reactor continuously at a flow rate of 1.8 g/h.

The results are shown in Table 1. Under the conditions employed, the formation of dimethyl disulphide (DMDS) is also accompanied by the formation of dimethyl polysulphides (DMPS) in which dimethyl trisulphide is the essential compound (>98%).

TABLE 1

| CATALYST | SULPHUR CONVERSION (%) | DMDS YIELD (%) | OUTPUT (g/h) | |
|---|---|---|---|---|
| | | | DMDS | DMPS |
| A21 resin | 100 | 80 | 376 | 63 |

TABLE 1-continued

| CATALYST | SULPHUR CONVERSION (%) | DMDS YIELD (%) | OUTPUT (g/h) | |
|---|---|---|---|---|
| | | | DMDS | DMPS |
| Triethylamine | 100 | 78.5 | 370 | 68 |

In both cases the weight composition of the DMDS+DMPS mixture leaving the reactor is the following:

DMDS=85%
DMPS=15%

B. Continuous synthesis of dimethyl disulphide from methyl mercaptan and sulphur with recycling of the dimethyl polysulphides Initially, the operation conditions are the same as those in the preceding tests (Section A), that is to say:

methyl mercaptan=960 g/h
sulphur=160 g/h
pressure=5.5 bars gauge
temperature=40° C.

After being separated from the reaction products, the dimethyl polysulphides (DMPS) formed are introduced into the reactor. It is noted that recycling of polysulphides results in a decrease in the yield of DMDS and in an increase in the DMPS content. To obtain a stable output in the reactor, the quantity of polysulphides to be recycled should be limited. Finally, a stationary production regime is established, with only a half of the quantity of the polysulphides recovered at the reactor exit being recycled, a quantity which corresponds to the production of polysulphides in the reactor.

These polysulphides contain a relatively high proportion of dimethyl polysulphides containing a number of sulphur atoms which is greater than 3.

The results of these tests are shown in the following table:

TABLE 2

| CATALYST | DMPS RECYCLING DMPS (g/h) | DMDS + DMPS (g/h) AT REACTOR EXIT | SULPHUR CONVERS. (%) | DMDS YIELD (%) | OUTPUT (g/h) | |
|---|---|---|---|---|---|---|
| | | | | | DMDS | DMPS |
| A21 resin | 162 | 559 | 99.5 | 50 | 235 | 162 |
| Triethylamine | 160 | 550 | 99.3 | 49 | 230 | 160 |

The weight composition of the DMDS+DMPS mixture leaving the reactor (test with A21 resin) is 42% of DMDS and 58% of DMPS, these polysulphides being distributed as follows:

S3=45%
S4=10.3%
S5=2.3%
S6=0.4%

The recycling of the dimethyl polysulphides formed in the reaction of oxidation of methyl mercaptan with sulphur results in a substantial decrease in the yield and the output of dimethyl disulphide.

EXAMPLE 2

Reversion of dimethyl polysulphides to dimethyl disulphide by the action of methyl mercaptan The reactor employed for the conversion of dimethyl polysulphides to dimethyl disulphide is a stainless steel, jacketed tubular reactor which has an internal diameter of 50 mm and contains a charge of 94 g of dry A21 resin. The reaction volume is 300 cm$^3$. In its lower part the reactor is equipped with feeds for introducing reactants (liquid methyl mercaptan and dimethyl polysulphide mixtures) and in its upper part it is connected to a pneumatic pressure-control valve and to a system for continually removing the liquid leaving the reactor.

The mixtures employed as reversion reactants are mixtures of dimethyl disulphide and of dimethyl polysulphides which have been obtained from the products recovered in the tests of Example 1, carried out in the stirred reactor in the presence of A21 resin, after removal of the hydrogen sulphide and of the methyl mercaptan which these products contained.

The quantities of methyl mercaptan introduced with these mixtures correspond to the excess of methyl mercaptan unconsumed in the synthesis of these DMDS+DMPS mixtures in the stirred reactor which was fed with a methyl mercaptan/sulphur molar ratio of 4.

The reactants (methyl mercaptan and mixtures containing the polysulphides) are introduced continuously into the tubular reactor, in which the pressure is maintained at 5.5 bars gauge using nitrogen and the temperature is controlled at 40° C.

The products recovered at the reactor exit are analyzed and the results obtained are listed in the following table:

TABLE 3

| Reference Example 1 | REACTANTS | | WEIGHT COMPOSITION DMDS + DMPS | | | |
|---|---|---|---|---|---|---|
| | DMDS + DMPS (g/h) | Methyl mercaptan (g/h) | Reactor entry | | Reactor exit | |
| | | | DMDS | DMPS | DMDS | DMPS |
| B | 430 | 798 | 42 | 58 | 94 | 6 |
| A | 438 | 528 | 85 | 15 | 98.5 | 1.5 |

Example 3

Production of dimethyl disulphide using the process according to the invention, by two reactors (primary reactor + finishing reactor) and an intermediate degasser The two reactors employed for the tests of Examples 1 and 2 are coupled, the stirred reactor being the primary reactor and the tubular reactor functioning as a finishing reactor. Between these two reactors is fitted a degassing system consisting of a jacketed vessel fitted with a stirrer and supporting a cooled column which makes it possible to recondense the methyl mercaptan which may be entrained with the hydrogen sulphide which must be degassed. The hydrogen sulphide dissolved in the crude product originating from the exit of the stirred reactor (primary reactor) is removed more or less efficiently, depending on the operating conditions (degasser temperature and pressure, temperature of the condensation column), while practically complete condensation of methyl mercaptan is effected. This equipment is supplemented by a pump placed between the exit of the degasser and the entry of the tubular reactor (finishing reactor), which enables this reactor to be fed with liquid product treated in the degasser.

The reactants (liquid methyl mercaptan at a flow rate of 960 g/h and liquid sulphur at a flow rate of 160 g/h) are introduced into the stirred reactor (primary reactor) with a reaction volume of 300 cm$^3$, which contains 20 g of dry Amberlyst A21 resin. The operating pressure is maintained at 5.5 bars gauge and the temperature at 40° C. The liquid leaving the bottom of the reactor is conveyed to the degasser to be treated. After treatment in the degasser the product is introduced into the tubular reactor (finishing reactor), which contains a charge of 94 g of dry Amberlyst A21 resin. The pressure in the reactor is 5.5 bars gauge and the temperature is 40° C. At the exit of the reactor the crude product is recovered and analyzed.

Tests were performed with different degrees of removal of the hydrogen sulphide in the degasser.

The results of these tests are shown in the following table:

TABLE 4

| PRIMARY REACTOR (exit) Weight composition (%) | | DEGASSER DEGREE OF REMOVAL of H$_2$S (%) | FINISHING REACTOR (exit) Weight composition (%) | |
|---|---|---|---|---|
| DMDS | DMPS | | DMDS | DMPS |
| 85 | 15 | 0 | 90 | 10 |
| 85 | 15 | 35 | 93 | 7 |
| 85 | 15 | 70 | 95 | 5 |
| 85 | 15 | 100 | 98.5 | 1.5 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. Process for the manufacture of dimethyl disulphide from methyl mercaptan and sulphur, comprising:
   (a) reacting methyl mercaptan and sulphur in a first reaction zone maintained at a pressure not above 50 bars but sufficient to maintain the methyl mercaptan in the liquid state, wherein the methyl mercaptan and sulphur are introduced in an excess of methyl mercaptan such that the methyl mercaptan/sulphur ratio is between 3 and 6 to selectively produce dimethyl disulphide and minimize methyl mercaptan recycling, and wherein said methyl mercaptan and sulphur are reacted at an elevated temperature in the presence of a catalyst that oxidizes mercaptans with sulphur,
   (b) treating products originating from the first reaction zone in a degassing zone, said products comprising dimethyl polysulphides, to selectively remove at least partially the dissolved hydrogen sulphide, wherein at least 50% of the hydrogen sulphide is removed, and
   (c) bringing the products originating from the degassing zone into contact with a catalyst in a second reaction zone to convert the dimethyl polysulphides with the excess methyl mercaptan.

2. Process according to claim 1, wherein the first reaction zone consists of a reactor or of a number of reactors arranged in parallel.

3. Process according to claim 1, wherein the methyl mercaptan is introduced into the first reaction zone in liquid form and the sulphur in solid or liquid form.

4. Process according to claim 1, wherein the operation is carried out in the first reaction zone at a temperature ranging from 25° C. to 150° C.

5. Process according to claim 1, wherein the second reaction zone comprises a number of reactors arranged in series, each preceded by an intermediate degasser.

6. Process according to claim 1, wherein the operation is carried out in the second reaction zone at a temperature ranging from 25° C. to 150° C., at an effective pressure up to 50 bars.

7. Process according to claim 1, wherein the catalysts employed in the two reaction zones are identical or different and are chosen from liquid or solid inorganic or organic basic agents, inorganic oxides and aluminosilicates.

8. Process according to claim 1, where said process further comprises the steps of:
 (d) treating products originating from the second reaction zone to completely remove dissolved hydrogen sulphide;
 (e) distilling the products of step (d) in a first column to separate unconsumed methyl mercaptan from the products of the second reaction zone;
 (f) recycling said unconsumed methyl mercaptan to said first reaction zone; and
 (g) distilling the products of step (e) in a second column to purify and separate dimethyl disulphide from unconverted dimethyl polysulphides.

9. Process according to claim 8, wherein the dimethyl polysulphides separated off in the second distillation column are conveyed back to the entry of the second reaction zone.

* * * * *

UNITED STATES PATENT AND TRADEMARK OFFICE
CERTIFICATE OF CORRECTION

PATENT NO. : 5,312,993

DATED : May 17, 1994

INVENTOR(S) : Emmanuel ARRETZ

It is certified that error appears in the above-identified patent and that said Letters Patent is hereby corrected as shown below:

Title page,
    change, [30] Foreign Application Priority Data from "Mar. 5, 1990 [FR] France..........0902715" to read --Mar. 5, 1990 [FR] France..........9002715--.

Signed and Sealed this

First Day of November, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,312,993
DATED : May 17, 1994
INVENTOR(S) : Emmanuel Arretz

It is certified that error appears in the above-indentified patent and that said Letters Patent is hereby corrected as shown below:

On the title page:

Item [73] Assignee "Elf Atochem S.A., Paris, France" to
-- Societe Nationale Elf Aquitaine (Production)--.

Item [30] Foreign Application Priority Data from
"Mar. 5, 1990 [FR] France.........0902715" to
--Mar. 5, 1990 [FR] France........9002715--.

Signed and Sealed this

Twelfth Day of September, 1995

Attest:

BRUCE LEHMAN

*Attesting Officer*     Commissioner of Patents and Trademarks